United States Patent [19]
Paul et al.

[11] Patent Number: 5,672,733
[45] Date of Patent: Sep. 30, 1997

[54] PROCESS FOR THE PREPARATION OF ISOBORNYL (METH) ACRYLATE

[75] Inventors: Jean-Michel Paul, Metz; Gérard Desire, Lens, both of France

[73] Assignee: Elf Atochem S.A., Puteaux, France

[21] Appl. No.: 575,952

[22] Filed: Dec. 21, 1995

[30] Foreign Application Priority Data

Dec. 22, 1994 [FR] France ................................ 94/15473

[51] Int. Cl.$^6$ .................................................... C07C 69/52
[52] U.S. Cl. ................................................. 560/220
[58] Field of Search ............................................ 560/220

[56] References Cited

FOREIGN PATENT DOCUMENTS 106956 5/1994 European Pat. Off. .
126293 10/1979 Japan .

OTHER PUBLICATIONS

Abstract, Database WPI, Wk. 8318, No. AN 83–42349, Derwent Publications Ltd., (JP-A-58 049 337, 23 Mar. 1983).
Abstract, Database WPI, Wk. 7423, No. AN 74–42542, Derwent Publications Ltd., (JP-A-49 013 158, 5 Feb. 1974).
Abstract, Database WPI, Wk. 7011, No. AN 70–17979, Derwent Publications Ltd., (DD7)–69586, 9 Oct. 1967).

Primary Examiner—Paul J. Killos
Attorney, Agent, or Firm—Millen, White, Zelano, & Branigan, P.C.

[57] ABSTRACT

This process for the preparation of isobornyl (meth)acrylate by reaction of (meth)acrylic acid with camphene consists in blending the reactants in a blending tank and in placing the mixture in contact with the catalyst in a cartridge which is separate from the blending tank.

Single figure.

11 Claims, 1 Drawing Sheet

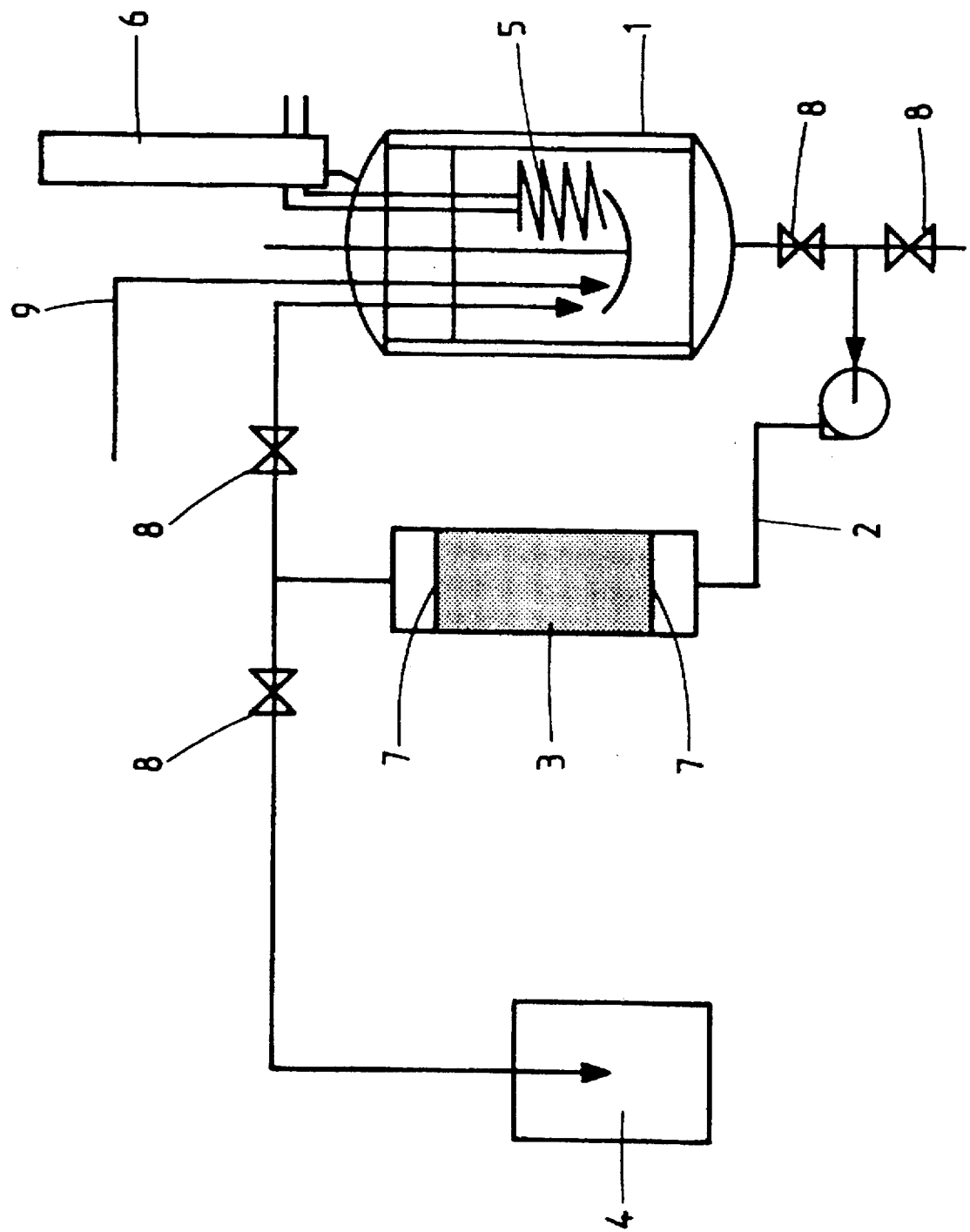

PROCESS FOR THE PREPARATION OF ISOBORNYL (METH) ACRYLATE

The present invention relates to a process for the preparation of isobornyl methacrylate and isobornyl acrylate of the formula

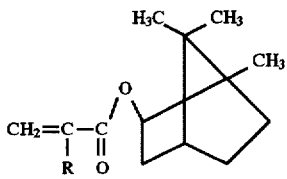

in which R is a hydrogen atom or a methyl radical.

U.S. Pat. No. 3,087,962 proposes a process for the preparation of isobornyl (meth)acrylate by reaction of (meth) acrylic acid with camphene of the formula

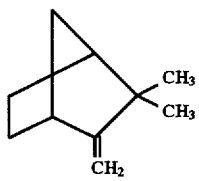

bearing in mind that a rearrangement then takes place. The process is carried out in the presence of a strong acid catalyst, such as sulphuric acid, or a Lewis acid, such as boron trifluoride. This process cannot be used on an industrial scale on account of its low yield, the corrosion of the reactors caused by the boron trifluoride and the need to separate out the catalyst, which is complicated.

In order to remedy the above, the Japanese patent application published under No. 58 049 337 proposes a process for the preparation of isobornyl (meth)acrylate of the same type as that referred to above, but in which the reaction is catalysed by a sulphonic strong cationic resin. The reaction is carried out in a batchwise manner in a mechanically stirred reactor or by direct passage of the reactants through a cartridge filled with resin. In the first embodiment, the resins may break on contact with the stirrer blades and a step of filtration of the resins is required before the distillation phase of the crude reaction product. In the second embodiment, the space velocities are low and the residence times on the resin are long. This results in poor dissipation of the heat generated by the reaction, which may give rise to a considerable rise in temperature within the charge of resin, with the concomitant risks of the formation of heavy by-products (of oligomeric type) which may recrack during distillation, or even, in extreme cases, of polymerization of the reaction mass.

SUMMARY OF THE INVENTION

The invention overcomes the drawbacks mentioned above by means of a process for the preparation of isobornyl (meth)acrylate which simplifies the procedure by dispensing with the filtration of the crude reaction product in order to separate out the resin before distillation, thereby making it possible to start the distillation phase immediately after the reaction, which places fewer mechanical constraints on the resins and which especially gives a better quality of crude reaction product with fewer heavy by-products and an improved material balance for the reaction, while at the same time having, compared with the process involving percolation of the reactants through a cartridge of resin, a higher space velocity and shorter residence times on the resin (preferably from 0.1 to 10 minutes with the technique according to the invention, whereas, in the prior document, this residence period was 60 minutes). The heat is thus easier to dissipate and the lower risk of an excessive temperature rise decreases the amount of heavy by-products formed and lowers the risk of polymerization.

The process according to the invention comprises blending (meth)acrylic acid and camphene in a stirred tank, in order to obtain a mixture, and in placing the mixture in contact with the catalyst in a cartridge which is separate from the blending tank. Furthermore, the reaction mixture is continuously cycled from the cartridge to the blending tank and back to the cartridge. In this way, only a fraction of the starting materials are converted per pass through the catalyst thereby permitting the heating and/or cooling requirements of the reaction to be controlled by heat exchange means associated with the blending tank.

There was no way of expecting that this technique, also referred to in the present account as "blended loop technique", would give, for the very specific reaction of camphene and (meth)acrylic acid involving a rearrangement, better yield and better selectivity and fewer heavy by-products, while at the same time lowering the risk of a polymerization. Nor was there any way of expecting that these good results would be obtained with a highs space velocity and a shortened residence time on the resin. The solid acid catalyst may be a Brönsted acid or a Lewis acid, or a macro-cross-linked strong cationic resin containing sulphonic acid groups (cf. Friedrich Hellferich, "Ion Exchange", Mc Graw Hill, N.Y., 1962, pp. 79 to 88). The sulphonic acid resins preferably have a pKa value of less than about 1.

The duration of contact of the mixture with the resin, expressed by the ration of the volume of swollen resin in the reaction mixture to the circulation flow rate of the mixture, is preferably between 0.1 and 10 minutes, more preferably between 1 and 3 or 1 to 2 minutes. In principal, multiple passes of the reaction mixture through the catalyst are required, preferably between about 24 and 2400 passes, especially between 80 and 240 passes.

The molar ratio of the (meth)acrylic acid to the camphene may be between ⅕ and ¼, and preferably between ⅔ and ½.

The reaction temperature is between 10° and 60° C., and preferably between 30° and 40° C., for isobornyl methacrylate, and between 10° and 50° C., and preferably between 10° and 30° C., for isobornyl acrylate.

The use of well-known solvents, such as cyclohexane, hexane and toluene, is possible.

It is recommended to use inhibitors, such as hydroquinone, hydroquinone monomethyl ether, highly sterically hindered phenols, or phenothiazine, in order to prevent the polymerization.

BRIEF DESCRIPTION OF THE DRAWING

The single figure in the attached diagram illustrates an installation which allows the process according to the invention to be carried out.

DETAILED DESCRIPTION OF THE DRAWING

The installation is composed:

of a blending tank (1) heated by a jacket and cooled by an internal coil (5). A condenser (6) is mounted above the tank, of a recycling loop (2) in which a resin cartridge (3) is mounted.

The resin is arranged between two supporting grills (7). Two sets of valves (8) make it possible
- to empty the tank (1) and the recycling loop (2),
- to direct the recycled flow to an intermediate container (4) during the first use of the resin or, under normal operating conditions, towards the blending tank (1).

The reactants may be introduced directly into the blending tank (1) via a conduit (9) or into the recycling loop (2).

The principal function of the blending tank is to provide the requisite heat exchange of the reaction mixture. Thus, the blending tank can be replaced by any conventional heat exchanger or combination thereof which can heat the reaction mixture at the beginning of the reaction and maintain the temperature to the end of the reaction. The heat exchanger must also be able to provide cooling as necessary, especially must also be able to provide cooling as necessary, especially during the initial phase of the reaction when the reaction is most exothermic.

During the first use of the acidic cationic ion exchange resin catalyst, fine particles of resin are removed and are purged into the intermediate tank 4. The associated reaction mixture which has served to "sweeten" the resin during the first use is then separated from the resin in tank 4 by any conventional means.

The example which follow illustrate the invention.

The present invention is carried out in practice according to the procedure below.

The invention uses acrylic acid or methacrylic acid and pure camphene or a camphene/tricyclene mixture.

The acrylic acid or methacrylic acid and camphene reactants (acid/camphene molar ratio: 1.05/1) are totally or partially introduced at the start into the blending tank, which is optionally cooled, and are then placed in forced circulation, by means of a pump through the resin cartridge.

The reaction mixture exiting the cartridge (3) is returned to the blending tank (1).

The temperature (40° C. for isobornyl methacrylate, 25° to 30° C. for isobornyl acrylate) is regulated by the heating jacket and by the cooling coil.

When all the reactants have not been introduced into the charge, the complement of reactants is added by running in an acid/camphene mixture over 1 to 2 hours, while controlling the temperature of the medium in the blending tank.

When all the reactants have been introduced, the reaction time is extended by 3 to 5 hours at the set temperature.

The crude reaction product is then distilled off under reduced pressure and the intermediate distillation fractions are recycled into the following operation.

The same resin cartridge is reused several times in succession.

EXAMPLE 1

226 g of methacrylic acid stabilized with 250 ppm of hydroquinone methyl ether (HQME), 340 g of camphene and 0.1 g of phenothiazine are introduced into the blending tank (1).

The mixture is then placed in circulation through a cartridge containing 63 g of dry Amberlyst 15 resin, at a circulation flow rate of 4 liters per hour.

The Amberlyst 15 resin swelds in the reaction medium. The volume of swollen wet resin is 75.6 cm$^3$.

The residence time per passage through the resin, calculated by the volume of swollen resin/circulation flow rate ratio, is 1.8 minutes.

The temperature is adjusted to 40° C. at the resin outlet, and the reaction time is 4 hours.

The crude reaction product which contains 8.9% methacrylic acid, 8.3% camphene, 81.3% isobornyl methacrylate and 1.5% heavy fractions is then distilled under reduced pressure.

The intermediate distillation fractions, rich in methacylic acid and camphene, are recycled into the following operation.

The same resin charge was used 6 times in succession without a decrease in performance.

The pure isobornyl methacrylate assays at 99.8 to 99.9% purity.

The balance of results for the operation are as follow:
degree of conversion of the methacrylic acid: 78%
degree of conversion of the camphene: 86%
yield of isobornyl methacrylate (relative to the methacrylic acid): 75%
selectivity (relative to the methacrylic acid): 96%

EXAMPLE 2

Example 1 is repeated, introducing only some of the reactants into the charge.

201.9 g of methacrylic acid stabilized with 250 ppm of HQME, 87 g of camphene, 0.15 g of pheneothiazine and 0.15 g of Topanol A (2,4-dimethyl-6-tert-butylphenol) are introduced into the blending tank. The mixture is placed in circulation for 10 minutes through the resin cartridge (63 g of dry Amberlyst 15 resin) at a flow rate of 4 liters per hour.

The remainder of the reactants is then introduced over 1 hour in the form of a 20/80 mixture of methacrylic acid/camphene (87 g of methacrylic acid; 348.2 g of camphene) while adjusting the temperature to 40° C.

When the introduced flow is complete, the reaction time at 40° C. is extended by 3 and a half hours.

The crude product, which contains 9% methacrylic acid, 8% camphene, 81% isobornyl methacrylate and 2% heavy products, is then purified as in Example 1.

EXAMPLE 3

Example 1 is repeated, replacing the methacrylic acid by acrylic acid.

234 g of acrylic acid stabilized with 200 ppm of HQME, 420 g of camphene and 0.13 g of phenothiazine are introduced into the blending tank.

The mixture is cooled to 16° C. and then circulated through the resin cartridge (63 g of dry Amberlyst 15 resin) at a circulation flow rate of 4 liters per hour.

The temperature of the blending tank is adjusted to 25°–30° C.

The reaction time is 4 hours.

The crude reaction mixture, which contains 6% acrylic acid, 7% camphene, 85% isobornyl acrylate and 2% heavy products, is then distilled under reduced pressure.

The material balance for the test is as follows:
acrylic acid conversion: 83%
camphene conversion: 89%
yield (relative to the acrylic acid): 79%
selectivity (relative to the acrylic acid): 94%

EXAMPLE 4

Example 2 is repeated, substituting the methacrylic acid by acrylic acid.

149.6 g of acrylic acid stabilized with 200 ppm of HQME, 84 g of camphene and 0.13 g of phenothiazine are charged into the blending tank.

The reaction mixture is cooled to about 16°–18° C. and then placed in circulation through the resin cartridge (63 g of dry Amberlyst 15).

After circulation for 10 minutes at a rate of 4 liters per hour, a flow of a 20/80 acrylic acid/camphene mixture (84 g/336 g) into the blending tank is commenced, while adjusting the temperature to between 25° and 30° C.

The complement of reactants is introduced over one hour.

The reaction time is then extended by 3 hours at 25°–30° C.

The crude reaction product, which contains 5.5% acrylic acid, 6% camphene, 85% isobornyl acrylate and 2 to 3% heavy products, is then purified by distillation under reduced pressure.

The degree of conversion/yield/selectivity values are identical to those of Test 3.

EXAMPLE 5

Comparison between the batchwise process (the reactants and the acidic resin are placed in contact in a mechanically stirred reactor) and the blended loop process:

(The conditions of temperature, of acid/camphene molar ratio and of overall reaction in the batchwise process are identical to those used in the blended loop process).

| | %  | | | |
|---|---|---|---|---|
| | methacrylic acid | camphene | isobornyl methacrylate | heavy products |
| isobornyl methacrylate | | | | |
| batchwise | 9.7 | 9.2 | 78.5 | 2 |
| blended loop | 8.9 | 8.3 | 81.3 | 1.5 |
| | acrylic acid | % camphene | isobornyl acrylate | heavy products |
| isobornyl acrylate | | | | |
| batchwise | 6.5 | 6 | 83 | 4.5 |
| blended loop | 6 | 6 | 85 | 3 |

Example 5 shows that, besides the practical advantages offered by the blended loop process (better control of the reaction exothermicity, elimination of the step of filtration of the resin), a crude reaction product is obtained which contains fewer heavy by-products liable to retrograde into acid which is difficult to separate from the isobornyl methacrylate, and especially from the isobornyl acrylate, during the distillation.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

The entire disclosure of all applications, patents and publications, cited above and below, and of corresponding French application 94/15.473, are hereby incorporated by reference.

What is claimed:

1. In a process for the preparation of isobornyl (meth) acrylate of the formula

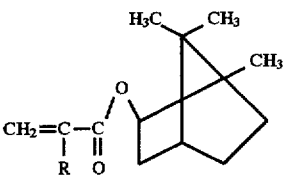

in which R is a hydrogen atom or a methyl radical, by reaction of (meth)acrylic acid, of the formula

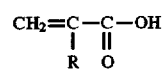

of the formula

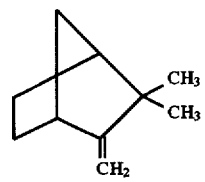

with camphene in the presence of, as a catalyst, an acidic cationic ion exchange resin, the improvement comprising blending (meth)acrylic acid and camphene in a blending tank in order to obtain a mixture and placing the mixture in contact with the catalyst in a cartridge which is separate from the blending tank.

2. A process according to claim 1, wherein the mixture is contacted with the resin, expressed by the ration of the volume of swollen resin in the reaction medium to the flow rate of passage of the mixture, between 0.1 and 10 minutes in a single pass.

3. A process according to claim 1, wherein the molar ration of the (meth)acrylic acid of the camphene is between 4:1 and 1:4.

4. A process according to claim 1, comprising placing the mixture in contact with the catalyst at a temperature between 10° and 60° C., for isobornyl (meth)acrylate, and between 10° and 50° C., and for isobornyl acrylate.

5. A process according to claim 2, wherein the mixture is contacted with the resin between 1 and 3 minutes in a single pass.

6. A process according to claim 3, wherein the molar ration is between 2:1 and 1:2.

7. A process according to claim 4, wherein the contact temperature for isobornyl (meth)acrylate is between 30° and 40° C.

8. In a process for the preparation of isobornyl (meth) acrylate of formula

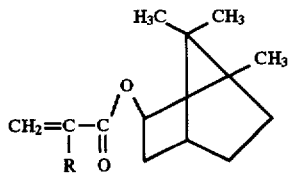

in which R is a hydrogen atom or a methyl radical, by reaction of (meth)acrylic acid, of the formula of the formula

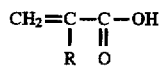

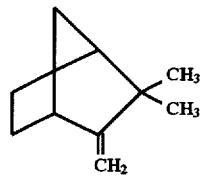

with camphene
in the presence of, as a catalyst, an acidic cationic ion exchange resin, forming a mixture of the (meth)acrylic acid and camphene starting materials and passing said mixture through a cartridge containing said resin in order to convert a partial amount of the starting materials to isobornyl (meth)acrylate, subjecting the resultant reaction mixture to heat exchange, then passing the resultant heat exchanged reaction mixture back to said cartridge to convert another partial amount of the starting materials and repeating the resultant cycle a plurality of times.

9. A process according to claim 8, wherein the mixture is contacted with the resin, expressed by the ratio of the volume of swollen resin in the reaction medium to the flow rate of passage of the mixture, between 0.1 and 10 minutes in a single pass and wherein between 24 and 2400 passes are conducted.

10. A process according to claim 9, where the time per pass is between 1 and 3 minutes, and between 80 and 240 passes are conducted.

11. A process according to claim 8, wherein after the first pass at least a portion of the reaction mixture is transferred to an intermediate tank to permit separation of catalyst fines from the reaction mixture.

* * * * *